(12) United States Patent
Hestad et al.

(10) Patent No.: US 8,382,840 B2
(45) Date of Patent: Feb. 26, 2013

(54) SPINAL IMPLANT DELIVERY METHODS AND DEVICES

(75) Inventors: Hugh D. Hestad, Edina, MN (US); John M. Dawson, Chaska, MN (US)

(73) Assignee: Zimmer Spine, Inc., Minneapolis, MA (US)

( * ) Notice: Subject to any disclaimer, the term of this patent is extended or adjusted under 35 U.S.C. 154(b) by 533 days.

(21) Appl. No.: 12/553,264

(22) Filed: Sep. 3, 2009

(65) Prior Publication Data

US 2011/0054548 A1 Mar. 3, 2011

(51) Int. Cl.
*A61F 2/44* (2006.01)
*A61B 17/88* (2006.01)

(52) U.S. Cl. .................. 623/17.16; 606/86 A

(58) Field of Classification Search ........ 623/1.11–1.23, 623/17.11–17.16; 606/86 R, 86 A, 90, 99–100, 606/248–249, 279, 914
See application file for complete search history.

(56) References Cited

U.S. PATENT DOCUMENTS

| | | | |
|---|---|---|---|
| 3,486,505 A | 12/1969 | Morrison | |
| 5,431,658 A | 7/1995 | Moskovich | |
| 5,484,437 A | 1/1996 | Michelson | |
| 5,505,732 A | 4/1996 | Michelson | |
| 6,019,787 A | 2/2000 | Richard et al. | |
| 6,042,582 A | 3/2000 | Ray | |
| 6,063,088 A | 5/2000 | Winslow | |
| 6,083,225 A | 7/2000 | Winslow et al. | |
| 6,267,763 B1 | 7/2001 | Castro | |
| 6,270,498 B1 | 8/2001 | Michelson | |
| 6,355,013 B1 * | 3/2002 | van Muiden | 604/96.01 |
| 6,432,130 B1 * | 8/2002 | Hanson | 623/1.11 |
| 6,478,800 B1 | 11/2002 | Fraser et al. | |
| 6,648,895 B2 | 11/2003 | Burkus et al. | |
| 6,656,213 B2 * | 12/2003 | Solem | 623/1.11 |
| 6,695,851 B2 | 2/2004 | Zdeblick et al. | |
| 6,770,074 B2 | 8/2004 | Michelson | |
| 6,899,727 B2 * | 5/2005 | Armstrong et al. | 623/1.12 |
| 6,955,661 B1 * | 10/2005 | Herweck et al. | 604/264 |
| 6,986,772 B2 | 1/2006 | Michelson | |
| 6,997,939 B2 | 2/2006 | Linder et al. | |
| 7,118,580 B1 | 10/2006 | Beyersdorff et al. | |
| 7,169,152 B2 | 1/2007 | Foley et al. | |
| 7,211,085 B2 | 5/2007 | Michelson | |
| 7,244,258 B2 | 7/2007 | Burkus et al. | |
| 7,314,468 B2 | 1/2008 | Michelson | |
| 7,465,305 B2 | 12/2008 | Liu et al. | |
| 7,547,308 B2 | 6/2009 | Bertagnoli et al. | |
| 7,547,309 B2 | 6/2009 | Bertagnoli et al. | |
| 7,569,054 B2 | 8/2009 | Michelson | |

(Continued)

*Primary Examiner* — Kevin T Truong
*Assistant Examiner* — Larry E Waggle, Jr.
(74) *Attorney, Agent, or Firm* — Seager Tufte & Wickhem LLC

(57) ABSTRACT

Systems and methods for implanting a spinal implant in a spinal column are disclosed. In one example, an illustrative system may include a delivery device including a proximal end region and a distal end region, a spinal implant releasably coupled to the distal end region of the delivery device, and a sleeve disposed about the spinal implant and at least a portion of the delivery device. In some cases, a distal portion of the sleeve may include a predetermined weakened region that may be configured to separate when a force is applied to the weakened region, which in some cases, may be applied with a pull string. In another example, a distal portion of the sleeve may be reverse folded upon itself such that the retractable sleeve rolls off of the spinal implant when the retractable sleeve is retracted.

17 Claims, 10 Drawing Sheets

U.S. PATENT DOCUMENTS

| | | | |
|---|---|---|---|
| 7,645,301 B2* | 1/2010 | Hudgins et al. | 623/17.12 |
| 7,909,871 B2* | 3/2011 | Abdou | 623/17.11 |
| 7,909,873 B2* | 3/2011 | Tan-Malecki et al. | 623/17.11 |
| 7,976,464 B2* | 7/2011 | Shluzas et al. | 600/219 |
| 8,118,844 B2* | 2/2012 | Anderson et al. | 606/279 |
| 2002/0058947 A1* | 5/2002 | Hochschuler et al. | 606/94 |
| 2003/0032964 A1* | 2/2003 | Watkins et al. | 606/93 |
| 2004/0186481 A1* | 9/2004 | Chern Lin et al. | 606/92 |
| 2004/0236272 A1* | 11/2004 | Lin et al. | 604/57 |
| 2004/0236306 A1* | 11/2004 | Lin et al. | 604/500 |
| 2004/0267271 A9* | 12/2004 | Scribner et al. | 606/92 |
| 2005/0182361 A1* | 8/2005 | Lennox | 604/103.01 |
| 2005/0234498 A1* | 10/2005 | Gronemeyer et al. | 606/192 |
| 2005/0261781 A1* | 11/2005 | Sennett et al. | 623/23.54 |
| 2006/0004435 A1* | 1/2006 | Burgermeister et al. | 623/1.15 |
| 2009/0012597 A1* | 1/2009 | Doig et al. | 623/1.13 |
| 2009/0043343 A1* | 2/2009 | Wales | 606/86 A |
| 2010/0049003 A1* | 2/2010 | Levy | 600/199 |

* cited by examiner

SPINAL IMPLANT DELIVERY METHODS AND DEVICES

FIELD

The present disclosure relates generally to spinal implants, and more particularly, to methods and devices for delivering a spinal implant to one or more spinal segments of a spinal column.

BACKGROUND

The spinal column is a highly complex system of bones and connective tissues that provides support for the body and protects the delicate spinal cord and nerves. The spinal column includes a series of vertebrae stacked one on top of the other, each vertebrae includes a vertebral body including an inner or central portion of relatively weak cancellous bone and an outer portion of relatively strong cortical bone. An intervertebral disc is situated between each vertebral body to cushion and dampen compressive forces experienced by the spinal column. A vertebral canal, called the foramen, containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column. For some disorders, it may be desirable to treat the disorder by implanting a prosthesis in the spinal column. However, in some cases, the prosthesis may have a relatively high coefficient of friction that can damage tissue and/or nerves adjacent to the treatment site during the implantation procedure. Accordingly, there is an ongoing need to provide alternative apparatus, devices, assemblies, systems and/or methods for implanting a prosthesis in a segment of a spinal column.

SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

The present disclosure relates generally to spinal implants, and more particularly, to methods and devices for delivering a spinal implant to one or more spinal segments of a spinal column. In one illustrative embodiment, a system for implanting a spinal implant in a spinal column is disclosed. The system may include a delivery device including a proximal end region and a distal end region, a spinal implant releasably coupled to the distal end region of the delivery device, and a sleeve disposed about the spinal implant and at least a portion of the delivery device. A distal portion of the sleeve may include a predetermined weakened region that is configured to separate when a force is applied to the weakened region. In some cases, the system may include a pull string that is configured to engage the sleeve adjacent to the weakened region and separate the weakened region of the sleeve when the pull string is pulled proximally. In some cases, a collar may be slidably disposed between the delivery device and the sleeve proximal of the spinal implant. In some cases, retraction of the collar relative to the delivery device may cause the sleeve to retract from the spinal implant.

In another illustrative embodiment, a method for implanting a spinal implant in a portion of a spinal column is disclosed. The method may include providing a delivery device including a proximal end region and a distal end region. The spinal implant may be releasably coupled to the distal end region of the delivery device and a retractable sheath may be disposed about the spinal implant and a portion of the delivery device. The method may also include positioning the spinal implant between two adjacent vertebrae of the spinal column with the delivery device, retracting the sheath from the spinal implant once the spinal implant is positioned between the two adjacent vertebrae, and releasing the spinal implant from the delivery device.

In another illustrative embodiment, a system for implanting a spinal implant in a spinal column is disclosed. The system may include a delivery device including a proximal end region and a distal end region, a spinal implant may be releasably coupled to the distal end region of the delivery device, and a retractable sleeve may be disposed about the spinal implant and at least a portion of the delivery device. In this embodiment, a distal portion of the retractable sleeve that is disposed about the spinal implant may be reverse folded upon itself. In some cases, the retractable sleeve may be configured to roll off of the spinal implant when the retractable sleeve is retracted.

BRIEF DESCRIPTION OF THE DRAWINGS

The disclosure may be more completely understood in consideration of the following detailed description of various illustrative embodiments of the disclosure in connection with the accompanying drawings, in which.

Figure 1:
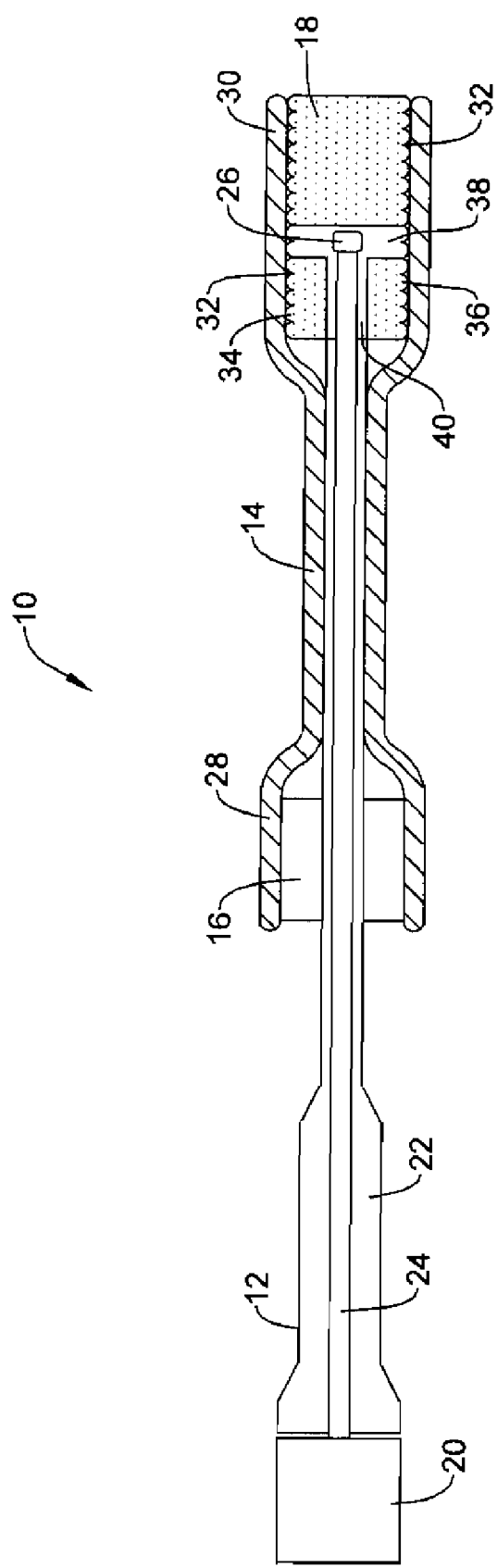
FIG. 1 is a side cross-sectional view of an illustrative embodiment of a system for implanting a spinal implant in a segment of a spinal column.

While the disclosure is amenable to various modifications and alternative forms, specifics thereof have been shown by way of example in the drawings and will be described in detail. It should be understood, however, that the disclosure is not limited to the particular embodiments described. On the contrary, the disclosure is considered to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 3.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings show several embodiments which are meant to be illustrative of the claimed invention. The drawings, which are not necessarily to scale, depict illustrative embodiments and are not intended to limit the scope of the disclosure.

While the following disclosure has been described with reference to relative terms, such as top, bottom, lateral, superior, inferior, and others, this is not meant to be limiting in any manner.

Figure 2:
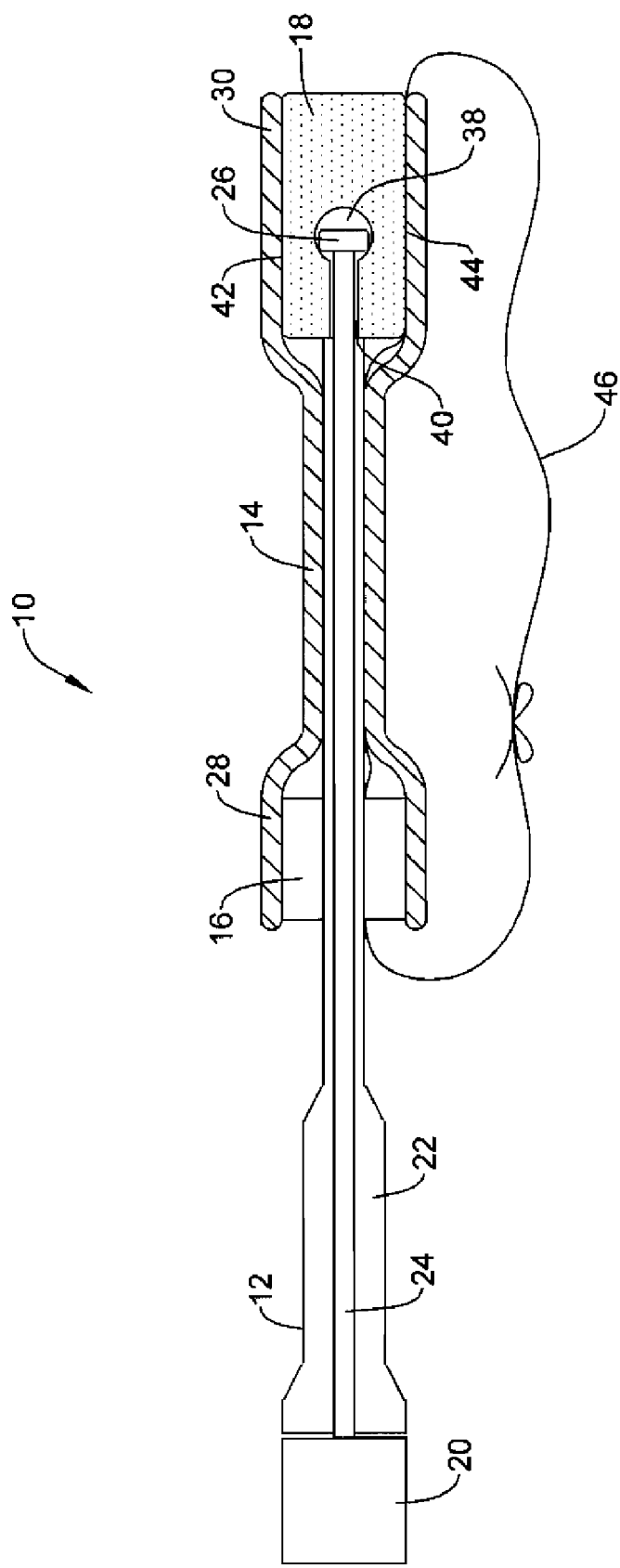
FIG. 2 is a top cross-sectional view of the illustrative system for implanting a spinal implant in a segment of a spinal column of FIG. 1.

Turning now to FIGS. 1 and 2, which are side and top cross-sectional views, respectively, of an illustrative embodiment of a system 10 for implanting a spinal implant 18 in a segment of a spinal column. In the illustrative embodiment, the system 10 may include a delivery instrument 12, a spinal implant 18 releasably coupled to a distal region of the delivery instrument 12, a sleeve 14 disposed about the spinal implant 18 and, in some cases, a portion of the delivery instrument 12, and an optional collar 16 slidably disposed about the delivery instrument 12.

In the illustrative embodiment, the spinal implant 18 may be configured to be inserted into a segment of a spinal column. For example, the spinal implant 18 may be configured to be inserted between adjacent vertebrae in a spinal column to replace at least a portion of a ruptured or otherwise diseased disc. Examples of spinal implants 18 may include Traebecular Metal™ products available from Zimmer Spine, Inc., which is the assignee of the present application, but it is contemplated that other suitable spinal implants 18 may be used. Spinal implants 18 may include any number of suitable materials, including for example, porous tantalum metal such as Traebecular Metal™, allograft bone, autograft bone, polyaryletheretherketone (PEEK), titanium, or any other synthetic or non-synthetic material that is commonly used for interbody devices or bone implants.

In some instances, the spinal implant 18 may include roughened surfaces which contact the vertebral bodies which assist in resisting migration of the spinal implant 18 when inserted between adjacent vertebrae. In some instances the roughened surfaces of the spinal implant 18 may be attributed, at least in part to the coefficient of friction of the material of the spinal implant 18. For instance, a spinal implant 18 formed of a porous tantalum metal, or other porous material, may have abrasive or rough exterior surfaces for contacting the vertebrae. As illustrated, the spinal implant 18 may include one or more surfaces having a pattern of ripples, grooves, teeth, ridges or undulations indicated by reference numeral 32, but this is not required. In some embodiments, the spinal implant 18 may include ripples, grooves, teeth, ridges or undulations 32 to increase stability and/or bonding of the spinal implant 18 to the segment of the spinal column. As illustrated in FIG. 1, a superior surface 34 of the spinal implant 18 and an inferior surface 36 of the spinal implant 18, which, when implanted, maybe in direct contact with a surface of the vertebrae of the spinal column, may include the ripples, grooves, teeth, ridges or undulations 32. As illustrated in FIG. 2, the lateral sides 42, 44 of the spinal implant 18 may be free of the ripples, grooves, teeth, ridges or other undulations 32. However, it is contemplated that the lateral surfaces 42,44 of the spinal implant 18 may include ripples, grooves, teeth, ridges or undulations 32, if desired. Additionally, the ripples, grooves, teeth, ridges or undulations 32 may have rounded edges, squared edges, angled edges, or any other suitable shape edge as desired. As illustrated, the ripples, grooves, teeth, ridges or undulations 32 may extend from a proximal end to a distal end of the spinal implant 18, but this is not required.

As illustrated, spinal implant 18 includes a passage 38 extending between the superior surface 34 and inferior surface 36. Passage 38 may allow the spinal implant 18 to be loaded with a material to facilitate bonding between the spinal implant 18 and the vertebrae of the spinal column. Example materials may include demineralized bone, Bone Morphogenic Proteins (e.g. BMP-2 or BMP-7), a patient's own bone marrow, or other suitable material. In some implantations, the passage 38 may be loaded with the material prior to insertion of the spinal implant 18 into the spinal column, or the passage 38 may be loaded after insertion of the implantation of the spinal implant 18, if desired. Further, while only one passage 38 is shown in FIG. 1, it is contemplated that one, two, three, four, five, or any number of passages may be provided in the spinal implant 18, as desired. Additionally, the spinal implant 18 may be configured to not have any passages, if desired.

In the illustrative embodiment, the spinal implant 18 may be configured to be releasably coupled to a distal region of the delivery instrument 12. The spinal implant 18 may include one or more features to provide a "locked" state for system 10, where the spinal implant is coupled to the distal region of the delivery instrument 12, and an "unlocked" state for system 10, where the spinal implant 18 can be released from the distal end of the delivery instrument 12. For example, the spinal implant 18 may be configured to include a channel 40 extending from a proximal end of the spinal implant 18 to passage 38, which as shown in FIGS. 1 and 2, has a greater diameter in one dimension than another dimension. For example, the diameter of channel 40 shown in side view of FIG. 1 may be greater than the diameter of channel 40 shown in the top view of FIG. 2. Further, the spinal implant 18 may include any number of other features to provide the desired releasability from the delivery instrument 12, such as, for example, threading, grooves, protrusions, or other interlocking features, as desired.

As illustrated, the delivery instrument 12 includes an outer tubular member 22 having a lumen and an inner member 24 rotatably disposed within the lumen of the outer member 22. In some cases, a proximal end region of the inner member 24 may be coupled to a hub portion 20 to assist in rotating the inner member 24 relative to the outer member 22. A proximal region of the outer member 22 may have an increased diameter, or one or more tapered portions, to define a handle portion for gripping by an operator or user. In this configuration, an operator or user may be able to grip the hub 20 and the increased diameter portion of the outer member 24 and may rotate one relative to the other to actuate the system 10 between the "locked" state and the "unlocked" state.

As illustrated, a distal end region of the inner member 24 may extend into channel 40 of the spinal implant 18 and include a knob portion 26 configured to releasably engage the spinal implant 18. As shown in FIGS. 1 and 2, the knob portion 26 of the inner member 24 may have a first diameter in a first dimension and a second different diameter in a second dimension. In the illustrative example, the dimensions may correspond to the dimensions of the channel 40 of the spinal implant 18. For example, as illustrated in FIGS. 1 and 2, the system 10 is in the "locked" state. In this state, the relatively larger diameter of the knob portion 26 is aligned with the relatively small diameter of the channel 40, shown in FIG. 2, so that the knob portion 26 cannot pass through the channel 40. However, a rotation of inner member 24 relative to the spinal implant 18 of about 90 degrees may align the relatively large diameter dimension of the knob portion 26 (shown in FIG. 2) with the relatively large diameter dimension of the channel 40 (shown in FIG. 1) to "unlock" the system 10. While in the "unlocked" state, the inner member 24 may be released from the spinal implant 18 such that the inner member 24 may be withdrawn from the spinal implant. In some embodiments, although not shown in FIGS. 1 and 2, the outer member 22 may be configured to engage a portion of the spinal implant 18 to prevent rotation of the spinal implant 18 when the inner member 24 is rotated, but this is not required.

The foregoing delivery instrument 12 and spinal implant 18 are merely exemplary embodiments of a delivery instrument and spinal implant and are not meant to be limiting in any manner. It is contemplated that any suitable delivery instrument and spinal implant may be used as desired.

In some cases, the spinal implant 18, such those including Traebecular Metal™ and PEEK, as well as those including the ripples, grooves, teeth, ridges or undulations 32, may have a relatively high coefficient of friction. The relatively high coefficient of friction may help to increase the stability and/or bonding of the spinal implant 18 to the segment of the spinal column, but can also make the spinal implant 18 difficult to implant. For example, the relatively high coefficient of friction of the spinal implant 18 can grab and/or damage adjacent tissue and/or nerves during the implantation process. In the illustrative embodiment, sleeve 14, which may have an outer surface with a lower coefficient of friction relative to the spinal implant 18, may be disposed about the spinal implant 18 and, in some cases, at least a portion of the delivery instrument 12. The relatively lower coefficient of friction of the sleeve 14 may, in some cases, help reduce damage to adjacent tissue and/or nerves during implantation of the spinal implant 18 between the vertebrae.

In some cases, the sleeve 14 may be formed from heat shrink tubing that may be heat shrunk along at least a portion of its entire length. As shown in FIGS. 1 and 2, the entire sleeve 14 has been heat shrunk over the delivery instrument 12 and spinal implant 18, but this is not required. In some embodiments, only the proximal end region 28 and the distal end region 30 of the sleeve 14 may be heat shrunk over the delivery instrument 12 and spinal implant 18.

In the illustrative embodiment, the sleeve 14 may include any number of suitable materials, such as for example, a fluropolymer resin such as PTFE, FEP, eTFE, or PFA. However, the sleeve 14 may include other materials such as biosorbable polymers which include polyesters, poly(amino acids), polyanhydrides, polyorthoesters, polyurethanes, and polycarbonates as well as PET (polyethylene Terephthalate) and Nylon. Furthermore, it is contemplated that the sleeve 14 may include any suitable material that is commonly used for sleeves, as well as any other suitable material, as desired.

As shown in FIG. 2, the system 10 may also include a pull string 46. As illustrated, the pull string 46 is looped around the sheath 14 so that it extends between the delivery instrument 12 and the sleeve 14, between the spinal implant 18 and the sleeve 14, and loops back around on the outside of the sleeve 14. The pull string 46 may be tied together with a knot as shown or, alternatively, may be formed as a continuous loop. In some cases, the pull string 46 may include a tab (not shown) attached thereto to aid an operator or user in grasping the pull string 46, but this is not required. This is just one example of a suitable pull string 46 and it is contemplated that other pull strings may be used. In operation, the pull string 46 may be configured to tear, rip, or separate at least the distal end region 30 of the sleeve 14 when the pull string 46 is pulled in a proximal direction.

In some embodiments, the system 10 may include an optional collar 16 disposed about a portion of the delivery instrument 12 proximal of the spinal implant 18. As illustrated, the optional collar 16 may be disposed between the delivery instrument 12 and the proximal end region 28 of the sleeve 14, which, in some cases, may be heat shrunk over the optional collar 16. In some embodiments, the collar 16 may be slidably and/or rotatably disposed about the delivery instrument 12 to facilitate retraction of the sleeve 14 from the spinal implant 18. In some cases, heat shrinking the sleeve 14 over the collar 16 may engage the sleeve 14 to the collar 16 such that retraction of the collar 16 relative to the delivery instrument 12 also retracts the sleeve 14. As shown in FIG. 2, the pull string 46 may be disposed between the optional collar 16 and the delivery instrument 12. However, it is contemplated that the pull string may be disposed between the optional collar 16 and sleeve 14, if desired.

Figure 3:
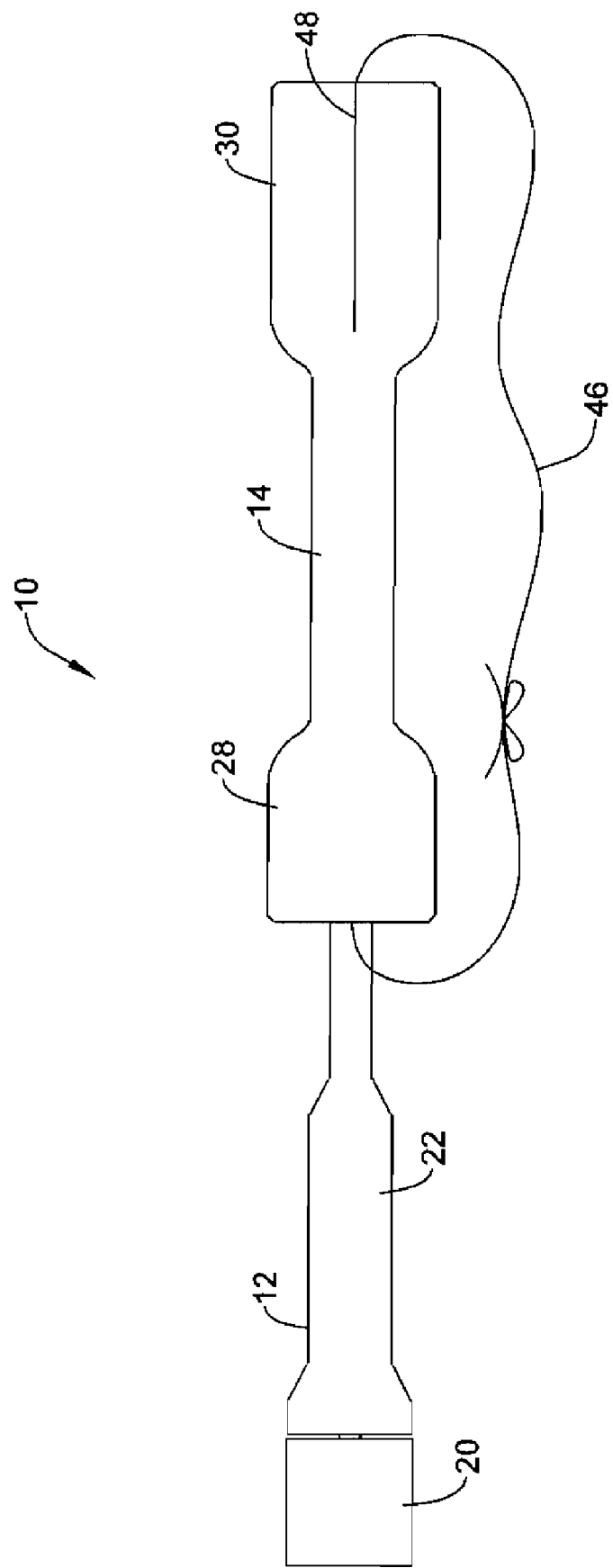
FIG. 3 is a side perspective view of the illustrative system for implanting a spinal implant in a segment of a spinal column of FIG. 1.
Figure 4:
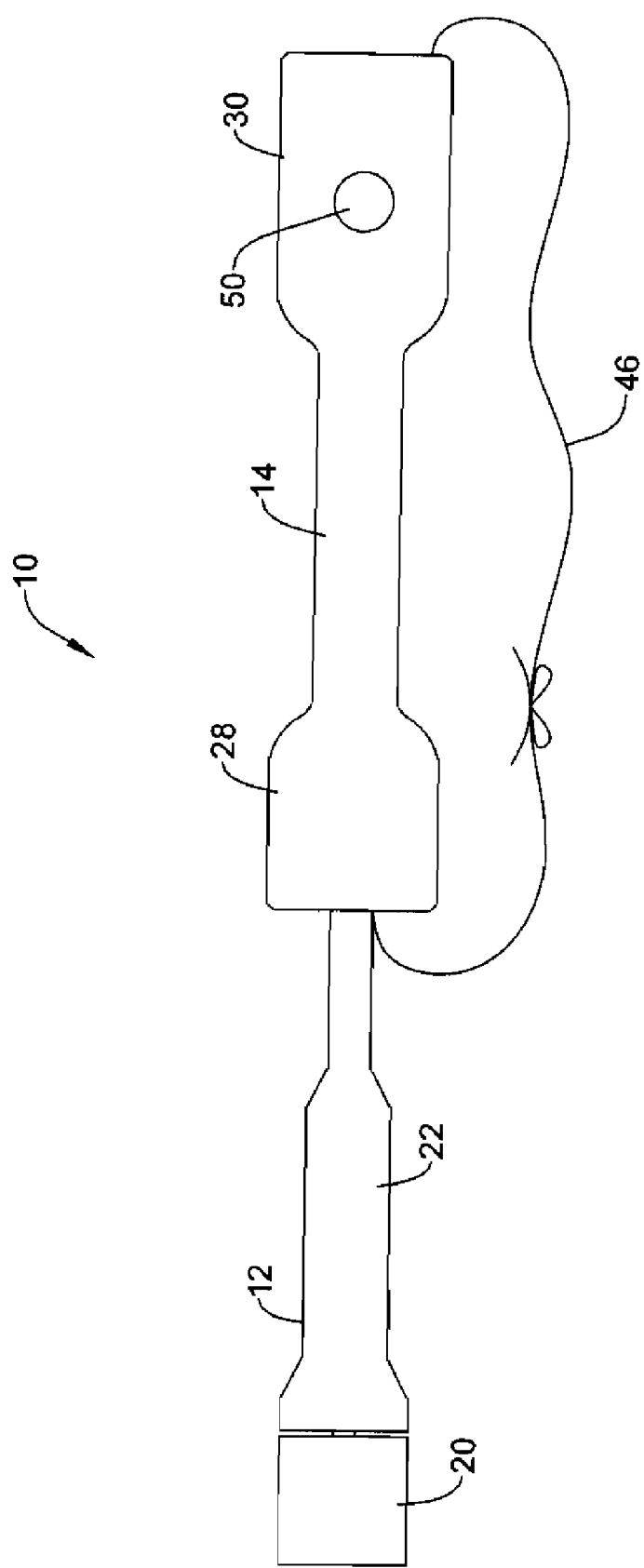
FIG. 4 is a top perspective view of the illustrative system for implanting a spinal implant in a segment of a spinal column of FIG. 1.

Referring now to FIGS. 3 and 4, which are side and top perspective views, respectively, of the illustrative system 10 shown in FIGS. 1 and 2. As illustrated in FIG. 3, the distal region 30 of the sleeve 14 may include a weakened region 48 or preferential tear line. The preferential tear lined or weakened region 48 may be, for example, a slit, a perforation, a skived portion, reduced thickness region, or the like that is predisposed to rip, tear, or separate when a force is applied to the sheath 14 adjacent to the weakened region. For example, when the illustrative pull string 46 is pulled proximally, a force may be exerted on the sleeve 14 adjacent to the weakened region 48. which may cause the weakened region to tear, rip, or separate and expose at least a portion of the spinal implant 18.

As shown in FIG. 3, the weakened region 48 may extend along the distal end region 30 of the sleeve 14. However, it is contemplated that the weakened region 48 may extend along the entire length of the sleeve 14 or along any suitable portion of the sleeve 14, as desired. In some embodiments, the weakened region 48 may be at a predetermined location on the sleeve 14. For example, as illustrated in FIG. 3, the weakened region 48 is positioned at a predetermined location on a lateral side of the sleeve 14. Further, it is contemplated that in some embodiments, the sleeve 14 may include multiple weakened regions similar to weakened region 48 or may not include any weakened regions, as desired. In the cases of multiple weakened regions, it is contemplated that a plurality of pull strings may be used to separate the multiple weakened regions. In the cases where the sleeve 14 is free of weakened regions, it is contemplated that the pull string 46 may still be provided and that the force of the pull string 46 on the sleeve 14 may rip, tear, or separate the sleeve 14.

Alternatively, it is contemplated that sleeve 14 may include any other features that may allow the sleeve 14 to expose the spinal implant 18. In one alternative example, a preformed slit and a retaining member (not shown) that may be woven or threaded through opposing edges to maintain the edges of the sleeve 14 together until the retaining member is removed. This is just one example.

As shown in FIG. 4, the distal region 30 of sleeve 14 may include an optional opening 50 corresponding to and aligned with the passage 38 (shown in FIGS. 1 and 2) in the spinal implant 18. In some cases, the opening 50 may facilitate filling the passage 38 of the spinal implant 18 with material to facilitate bonding of the spinal implant 18 to the spinal column, as discussed previously. It is contemplated that the sleeve 14 may include an opening 50 in the superior surface of the sleeve 14, the inferior surface of the sleeve 14, or both the superior surface and inferior surface of the sleeve 14, as desired.

FIGS. 5-8 are schematic views showing an illustrative method for implanting the spinal implant 18 in a segment of a spinal column with the illustrative system of FIGS. 1 and 2. In some embodiments, the spinal implant 18 may be preloaded with material to facilitate bonding, as discussed previously, prior to implanting the spinal implant 18.

Figure 5:
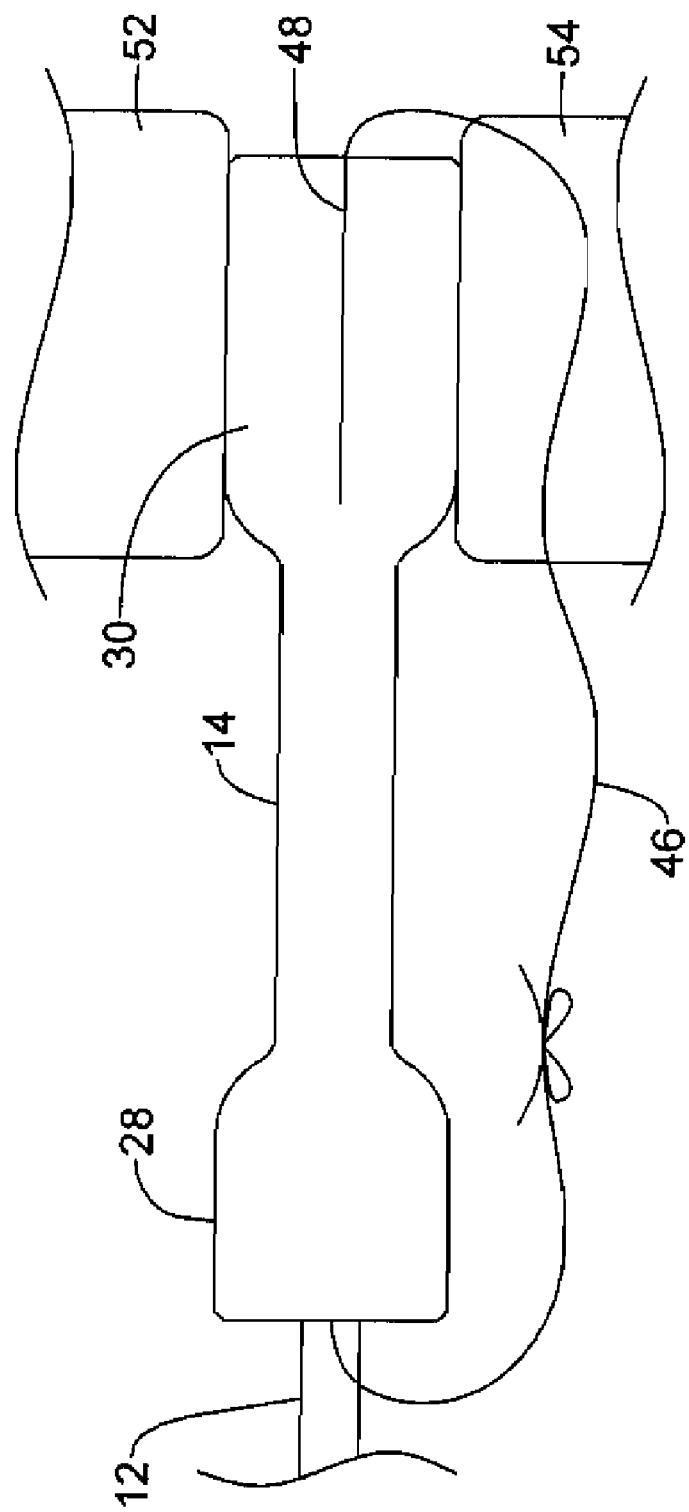
FIGS. 5-8 are schematic views showing an illustrative method for implanting a spinal implant in a segment of a spinal column with the illustrative system of FIG. 1.

As shown in FIG. 5, the distal region of system 10, such as the distal end region 30 of the sleeve 14 and the spinal implant 18, may be inserted between two adjacent vertebrae, such as vertebrae 52 and 54. The presence of the sleeve 14 between the superior surface 34 and/or inferior surface 36 of the spinal implant 18 and the adjacent vertebrae may prevent direct contact between the superior and/or inferior surfaces 34/36 and the end plates of the adjacent vertebrae as the spinal implant 18 is moved relative to the vertebrae into place. Thus, the presence of the sleeve 14, which may provide a interface with the end plates of the vertebrae having a lower coefficient of friction than an interface between the spinal implant 18 and the end plates of the vertebrae, may protect against the roughened surfaces of the spinal implant 18 from grabbing and/or damaging adjacent tissue and/or nerves during the implantation process. The distal region of system 10 may be positioned such that the weakened region 48 of sleeve 14 is positioned on a lateral side and such that the ripples, grooves, or undulations 32 are positioned on the superior and inferior surfaces.

Figure 6:
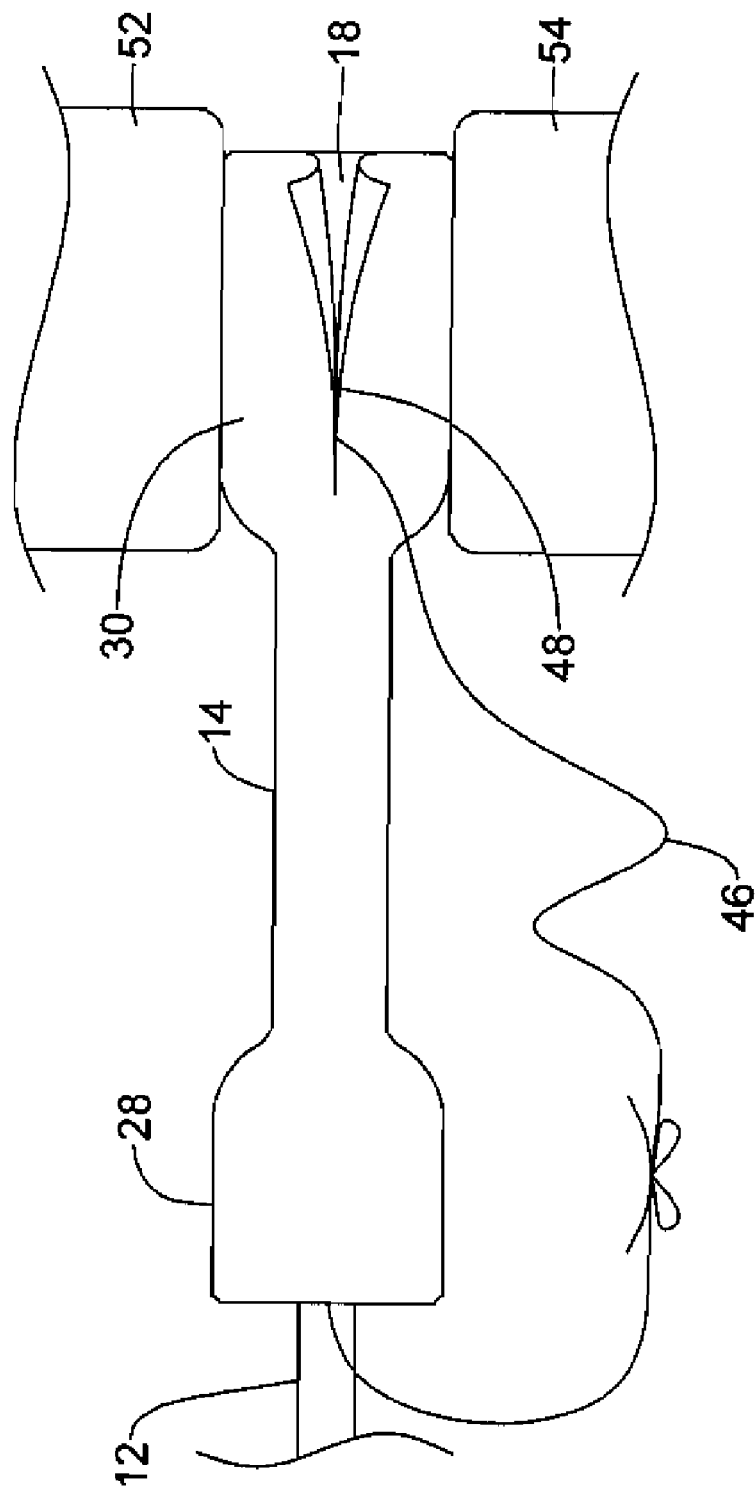
Figure 7:
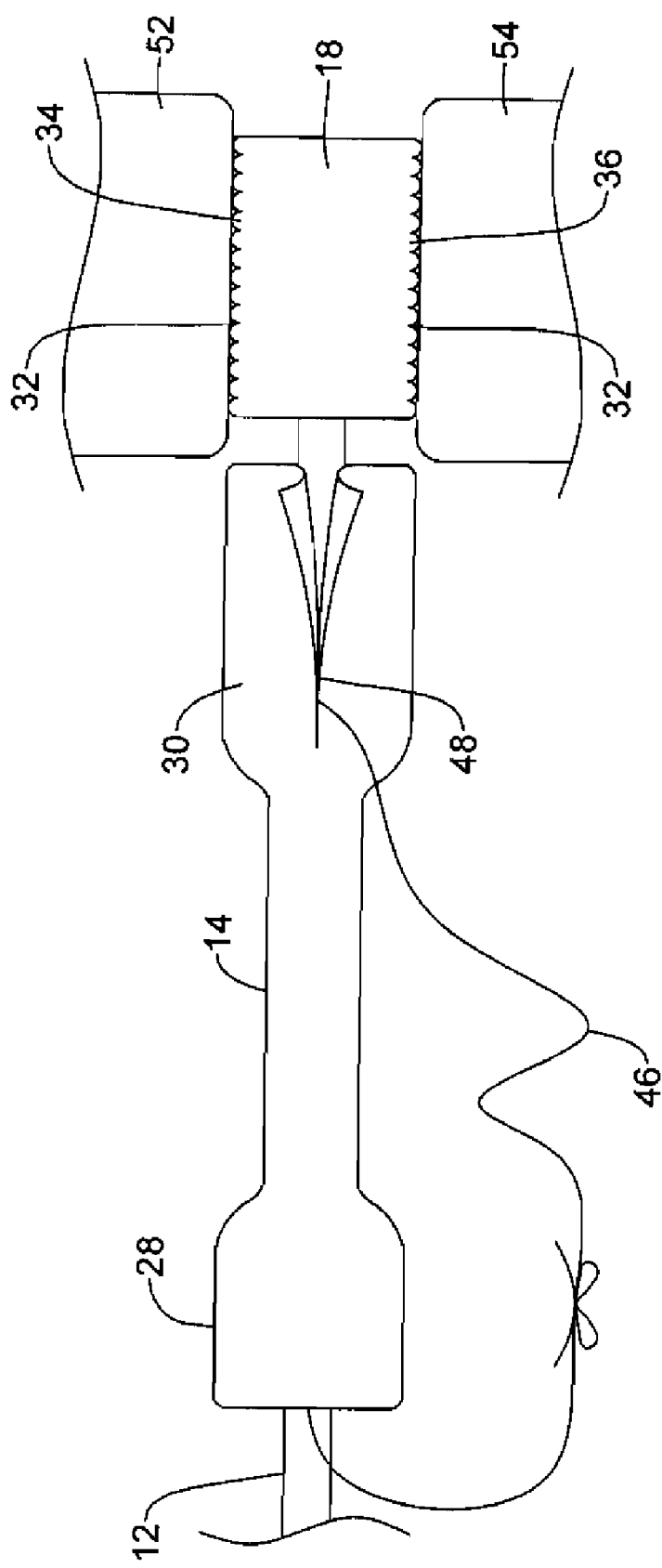

As illustrated in FIG. 6, the pull string 46 may be pulled in a proximal direction exerting a force on the weakened region 48 of the sleeve causing the weakened region 48 to rip, tear, or separate. Then, with the distal region of the sleeve 30 separated, as shown in FIG. 7, the sleeve 14 may be retracted from the spinal implant 18 by pulling the collar 16 and/or sleeve 14 in a proximal direction relative to the delivery instrument 12. As the sleeve 14 is retracted, the spinal implant 18 is exposed between vertebrae 52 and 54 such that the ripples, grooves, teeth, ridges or undulations 32 of the posterior surface 34 and anterior surface 36 contact the vertebrae 52 and 54, as shown in FIG. 7.

Figure 8:
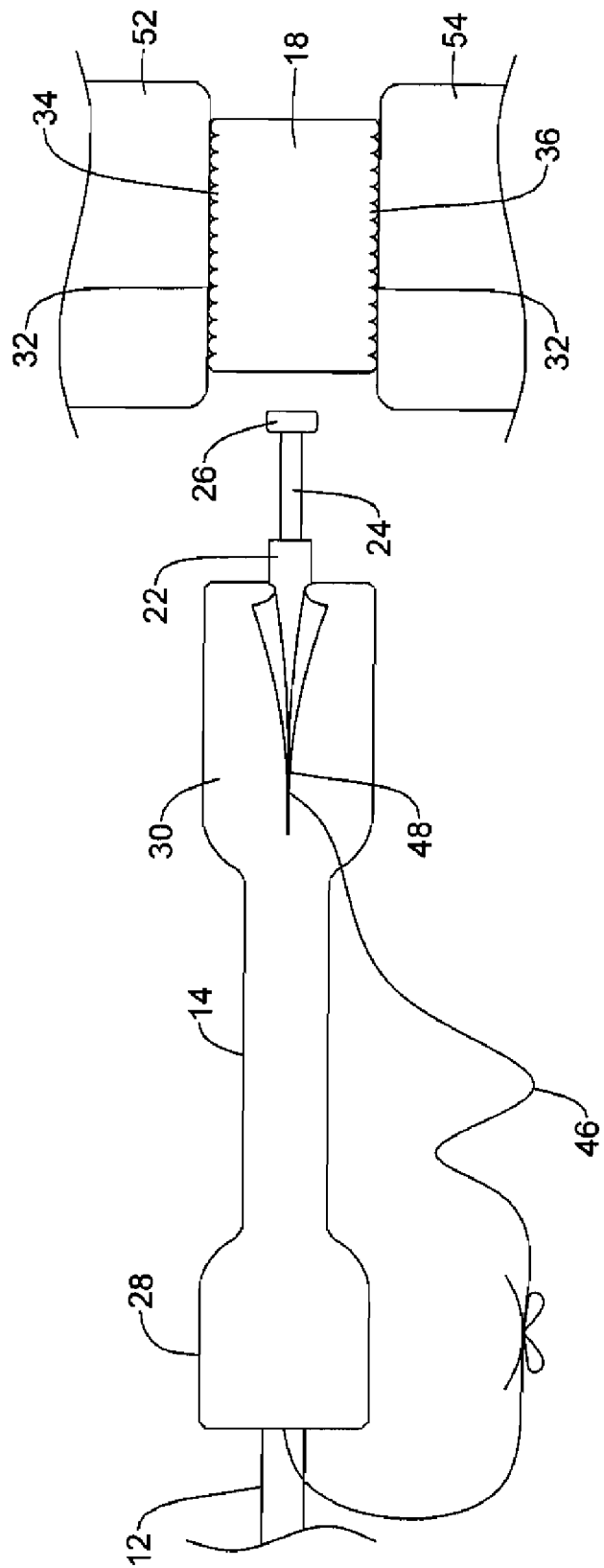

Next, as shown in FIG. 8, the spinal implant 18 may be released or deployed from the delivery instrument 18 such that the delivery instrument 12 and sleeve 14 can be removed from the patient leaving the spinal implant 18 between vertebrae 52 and 54 of the spinal column. In some embodiments, the spinal implant 18 may be released by rotating the inner member 24 relative to the outer member 22 to, for example, move the system from the "locked" state to the "unlocked" state, as discussed above. However, it is contemplated that other suitable methods and systems may be used to release the spinal implant 18 from the delivery instrument 12, as desired.

Figure 9:
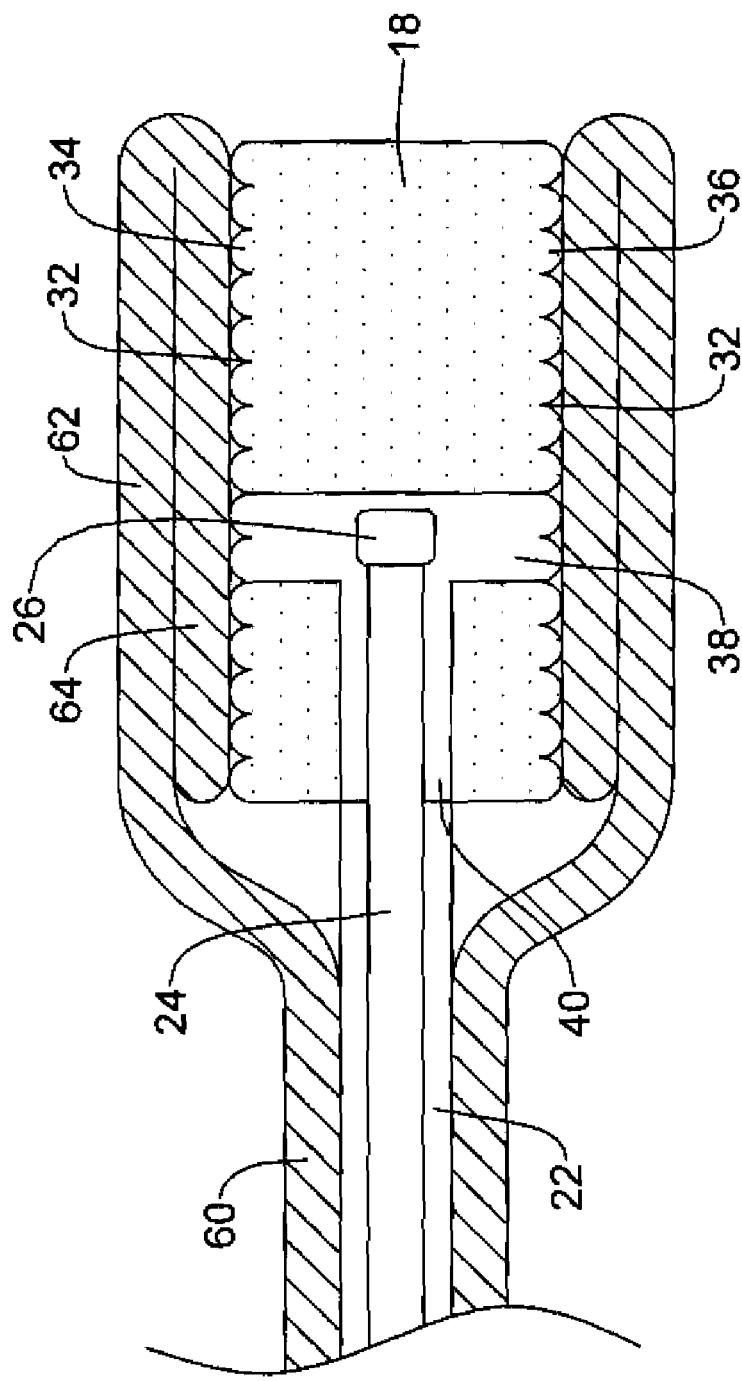
FIGS. 9 and 10 are side cross-sectional views of an alternative distal end region that may be used with the illustrative system of FIG. 1.
Figure 10:
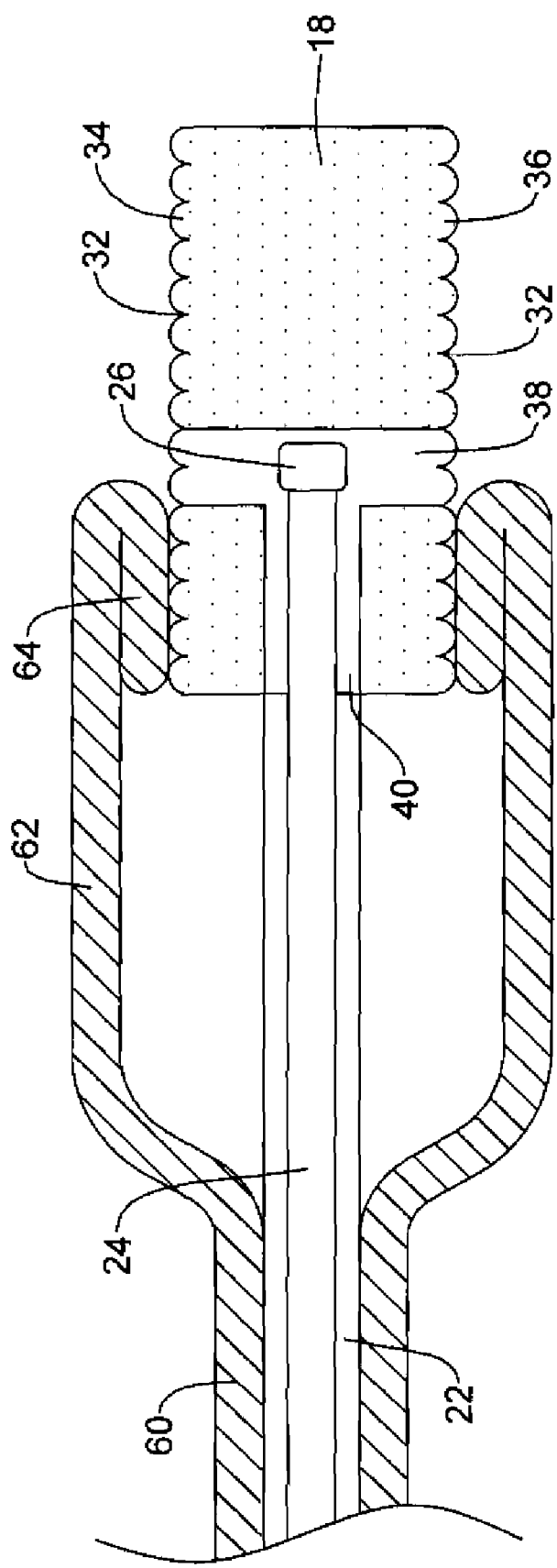

FIGS. 9 and 10 are side cross-sectional views of an alternative sleeve 60 that may be used with the illustrative system of FIGS. 1 and 2. In the illustrative embodiment, the sleeve 60 may be disposed about the spinal implant 18 and at least a portion of the delivery instrument 12. The portion of the sleeve 60 disposed about the spinal implant 18 may be reverse folded or, in other words, folded upon itself. In this example, sleeve 60 may be folded such that region 62 is folded onto region 64 of the sleeve 60. In this folded configuration, the end of sleeve 60 may be adjacent a proximal end of the spinal implant 18 and extend distally to a distal end of the spinal implant 18 where the sleeve 60 folds back onto itself and extends in a proximal direction. As the sleeve 60 is retracted from the spinal implant 18, the distal end region of the sleeve may roll off of the spinal implant 18 in a rolling motion such that there is no sliding contact between the surfaces of the sleeve 60 and the spinal implant 18.

Although not shown in FIGS. 9 and 10, it is contemplated that the sleeve 60 may include a weakened region and/or pull sting, similar to embodiments discussed above, if desired.

It should be understood that this disclosure is, in many respects, only illustrative. Changes may be made in details, particularly in matters of shape, size, and arrangement of steps without exceeding the scope of the disclosure. The invention's scope is, of course, defined in the language in which the appended claims are expressed.

What is claimed is:

1. A system for treating a spine, the system comprising:
 a delivery device including a proximal end region and a distal end region;
 a non-expandable spinal implant releasably coupled to the distal end region of the delivery device; and
 a sleeve disposed about the non-expandable spinal implant and at least a portion of the delivery device, wherein a distal portion of the sleeve includes a predetermined weakened region that is predisposed to separating when a force is applied to the sleeve adjacent to the weakened region.

2. The system of claim 1 further comprising a pull string coupled to the sleeve, wherein the pull string is configured to separate the weakened region of the sleeve when the pull string is pulled proximally.

3. A system for treating a spine, the system comprising:
 a delivery device including a proximal end region and a distal end region;
 a spinal implant releasably coupled to the distal end region of the delivery device;
 a sleeve disposed about the spinal implant and at least a portion of the delivery device, wherein a distal portion of the sleeve includes a predetermined weakened region that is predisposed to separating when a force is applied to the sleeve adjacent to the weakened region; and
 a pull string coupled to the sleeve, wherein the pull string is configured to separate the weakened region of the sleeve when the pull string is pulled proximally,
 wherein the delivery device includes an actuatable collar coupled to the sleeve such that actuation of the collar causes the sleeve to retract from the spinal implant.

4. The system of claim 3 wherein the pull string is disposed between the collar and an elongate shaft of the delivery device.

5. The system of claim 3 wherein the sleeve is heat shrunk about the spinal implant and the collar.

6. The system of claim 1 wherein the sleeve includes a lubricious material.

7. The system of claim 1 wherein the weakened region is a slit.

8. The system of claim 1 wherein the weakened region is a skived region.

9. The system of claim 1 wherein the weakened region is a perforation.

10. The system of claim 1 wherein the non-expandable spinal implant includes a passage configured to receive a material to facilitate bonding of the non-expandable spinal implant to the spinal column, wherein the sleeve has an opening corresponding to the passage of the non-expandable spinal implant.

11. The system of claim 1 wherein the delivery device includes an outer member and an inner member, wherein the inner member is rotatably disposed in a lumen of the outer member.

12. The system of claim 11 wherein the non-expandable spinal implant is releasable from the delivery instrument by rotating the inner member relative to the outer member.

13. The system of claim 1 wherein the non-expandable spinal implant includes a porous tantalum metal material.

14. A system for treating a spine, the system comprising:
a delivery device including a proximal end region and a distal end region;
a non-expandable spinal implant releasably coupled to the distal end region of the delivery device, the non-expandable spinal implant having vertebral-contacting exterior surfaces having an implant coefficient of friction; and
a sleeve disposed about the non-expandable spinal implant and at least a portion of the delivery device, wherein a distal portion of the sleeve includes a predetermined weakened region that is predisposed to separating when a force is applied to the sleeve adjacent to the weakened region, the sleeve having an outer surface with a sleeve coefficient of friction, the sleeve coefficient of friction being lower than the implant coefficient of friction, and the sleeve substantially preventing contact between the vertebral-contacting exterior surfaces of the non-expandable spinal implant prior to separation of the sleeve.

15. The system of claim 14, wherein the non-expandable spinal implant includes porous tantalum metal.

16. The system of claim 14, wherein one or more of the vertebral-contacting exterior surfaces of the non-expandable spinal implant are roughened.

17. The system of claim 14, wherein the one or more roughened vertebral-contacting exterior surfaces of the non-expandable spinal implant includes a pattern of ripples, grooves, teeth, ridges or undulations.

* * * * *

UNITED STATES PATENT AND TRADEMARK OFFICE
CERTIFICATE OF CORRECTION

PATENT NO. : 8,382,840 B2
APPLICATION NO. : 12/553264
DATED : February 26, 2013
INVENTOR(S) : Hugh D. Hestad et al.

It is certified that error appears in the above-identified patent and that said Letters Patent is hereby corrected as shown below:

In the Specification

Column 3, Line 9: delete "3.5" and insert -- 1.5 --.

Signed and Sealed this
Third Day of December, 2013

Margaret A. Focarino
*Commissioner for Patents of the United States Patent and Trademark Office*